United States Patent [19]

Lin et al.

[11] Patent Number: 5,214,136
[45] Date of Patent: May 25, 1993

[54] ANTHRAQUINONE-DERIVATIVES OLIGONUCLEOTIDES

[75] Inventors: Kuei-Ying Lin, Fremont; Mark Matteucci, Burlingame, both of Calif.

[73] Assignee: Gilead Sciences, Inc., Foster City, Calif.

[21] Appl. No.: 482,941

[22] Filed: Feb. 20, 1990

[51] Int. Cl.$^5$ .................. C07H 17/00; A61K 31/70
[52] U.S. Cl. ........................... 514/44; 536/24.5
[58] Field of Search ................. 536/27; 514/44

[56] References Cited

PUBLICATIONS

Chem. Abst. 114: 78183d, 1991.
Chem. Abst. 114: 43432g, 1991.
Ogilvie et al., *Pure and Appl. Chem.* (1987) 59(3):325–330.
Froehler et al., *Nucleic Acids Res.* (1986) 14(13):5399–5407.
Asseline et al., *Tetrahedron Letters* (1989) 30(19): 2521–2524.
Bayard et al., *Biochemistry* (1986) 25:3730–3736.
Lemaitre et al., *Nucleosides and Nucleotides* (1987) 6 (1&2):311–315.
Zuckerman et al., *Nucleic Acids Res.* (1987) 15(13):5305–5321.
Lancelot et al., *Biochemistry* (1985) 24:2521–2529.
Asseline et al., *Proc. Natl. Acad. Sci.* (1984) 81:3297–3301.
Mori et al., *FEBS Letters* (1989) 249(2):213–218.
van der Krol et al., *Biotechniques* (1988) 6(10):958–976.
Stein et al., *Cancer Res.* (1988) 48:2659–2668.

*Primary Examiner*—John W. Rollins
*Attorney, Agent, or Firm*—Morrison & Foerster

[57] ABSTRACT

Oligonucleotide sequences modified by conjugation to at least one unsubstituted or substituted anthraquinone at other than the 5' terminus have favorable properties in enhancing hybridization to target DNA or RNA without loss of specificity and show enhanced stability to nucleases.

5 Claims, No Drawings

ANTHRAQUINONE-DERIVATIVES OLIGONUCLEOTIDES

TECHNICAL FIELD

The invention relates to oligonucleotides in forms which have been modified so as to enhance their hybridization ability and stability with respect to nucleases without decreasing their specificity for target complementary RNA or DNA. More precisely, the invention concerns oligonucleotides coupled to at least one anthraquinone residue.

BACKGROUND ART

The oligonucleotides of the invention are intended, in general, for application to an approach which has come to be known as "antisense" therapy.

The general principles of antisense therapy are now well recognized. Most diseases and undesirable conditions in humans and animal subjects are mediated by specific DNA or RNA sequences which, if inactivated, would no longer be able to facilitate the progress of the disease. The antisense approach provides DNA or RNA oligomers, or their analogs, which are capable of specific binding to the undesirable nucleic acid sequences. These materials can be supplied directly or generated in situ, and may be conventional oligomers, or are more commonly oligomers having properties which make them, for example, resistant to nucleases or more capable of hybridization to the desired target. The hybridization may be effected by providing oligomers having sequences which result in conventional base-pairing, or these may recognize double-stranded DNA by binding to the major or minor grooves which are present in the double helix. Whatever the ultimate strategy, it is desirable to provide oligomers with physiological properties which render them more effective.

The art provides a number of approaches whereby modified oligonucleotides are used in antisense applications. For example, in order to provide enhanced stability in vivo, through resistance to endogenous nucleases, oligomers have been synthesized with alternative linkages other than the conventional phosphodiester linkage. Among these are the methylphosphonates wherein one of the phosphorous-linked oxygens has been replaced by methyl; phosphorothioates, wherein sulfur replaces one of the oxygens; and various amidates, wherein $NH_2$ or organic amine derivatives, such as morpholidates or piperazidates, replace an oxygen. Also carbonate and carbamate linkages have been employed, as well as those involving sulfur rather than oxygen as a linking substituent.

In addition, modifications have been employed wherein the oligonucleotides are conjugated with a lipophilic group to enhance cell permeation capability. Inclusion of intercalators and chelators which enhance the ability of the oligonucleotide to bind the target DNA or RNA is also known. These substituents have been attached to the 5' end of preconstructed oligonucleotides using amidite or H-phosphonate chemistry, as described by Ogilvie, K. K., et al., *Pure and Appl Chem* (1987) 59:325, and by Froehler, B. C., Nucleic Acids Res (1986) 14:5399. Intercalators have also been attached to the 3' end of oligomers, as described by Asseline, U., et al., *Tet Lett* (1989) 30:2521. This last method utilizes 2,2'-dithioethanol attached to a solid support to displace diisopropylamine from a 3' phosphonate bearing the acridine moiety and is subsequently deleted after oxidation of the phosphorus. Other substituents have been bound to the 3' end of oligomers by alternate methods, including polylysine (Bayard, B., et al., *Biochemistry* (1986) 25:3730; Lemaitre, M., et al., *Nucleosides and Nucleotides* (1987) 6:311) and, in addition, disulfides have been used to attach various groups to the 3' terminus, as described by Zuckerman, R., et al., *Nucleic Acids Res* (1987) 15:5305. It is known that oligonucleotides which are substituted at the 3' end show increased stability and increased resistance to degradation by exonucleases (Lancelot, G., et al., *Biochemistry* (1985) 24:2521; Asseline, U., et al., *Proc Natl Acad Sci USA* (1984) 81:3297). A recent report by Mori, K., et al., *FEBS Lett* (1989) 249:213-218, describes oligonucleotides coupled to anthraquinone at the 5' terminus. The coupled oligomers exhibit anti HIV activity in vitro; and the inclusion of the anthraquinone residue appears to raise the melting temperature. The advantage of this 5' derivatization is said to be the activity of the anthraquinone as an oxidizing agent and to produce radicals.

The general approach to constructing various oligomers useful in antisense therapy has been reviewed by vander Krol, A.R., et al., *Biotechniques* (1988) 6:958-976, and by Stein, C. A., et al., Cancer Res (1988) 48:2659-2668, both incorporated herein by reference.

The present invention provides oligonucleotides which are coupled to at least one anthraquinone moiety at other than the 5' terminus; the inclusion of this moiety is capable of enhancing the ability of the oligomer to hybridize specifically to target sequences without loss of specificity. In addition, the anthraquinone can serve as a marker and can stabilize the oligomer with respect to nuclease degradation.

DISCLOSURE OF THE INVENTION

The invention is directed to oligonucleotides derivatized to anthraquinone which can be employed in therapy, for example through antisense or other mechanisms, or which can be used in a diagnostic method which involves binding to specific target oligonucleotides.

Thus, in one aspect, the invention is directed to oligonucleotides coupled to at least one anthraquinone at other than the 5' terminus which anthraquinone is unsubstituted or which optionally is substituted with one or more substituents which do not interfere with the coupling of the anthraquinone to the oligonucleotide or with its stability-conferring properties. Examples of such substituents include alkyl (1-6C)-substituted alkyl with conventional functional groups such as hydroxyl, carboxyl or the esters amides or salts thereof; amino groups; sulfhydryl groups; and halo substituents, such as iodo, bromo, chloro, or fluoro. The substituents may be in any position of the ring, and may be single or multiple. The nature of the substituents is limited only by the availability of the compounds and their noninterference with the basic properties conferred by the anthraquinone nucleus on the oligonucleotide to which it is conjugated. The conjugation to the oligonucleotide is preferably through a beta position of the anthraquinone and may incorporate a linker moiety between the anthraquinone and the oligomer.

In other aspects, the invention is directed to pharmaceutical compositions containing the anthraquinone-derivatized oligomers of the invention and to methods to bind target DNA using these compounds and compositions.

MODES OF CARRYING OUT THE INVENTION

Definitions

As used herein, "antisense" therapy refers to administration or in situ generation of DNA or RNA oligomers or their derivatives which bind specifically to a target nucleic acid sequence. The binding may be by conventional base pair complementarity, or, for example, in the case of binding to DNA duplexes, through specific interactions in the major groove of the double helix. In general, "antisense" refers to the range of techniques generally employed under this description in the art, and includes any therapy which relies on specific binding to oligonucleotide sequences.

"Oligomers" or "oligonucleotides" includes sequences of more than one nucleotide and specifically includes short sequences such as dimers and trimers.

The oligonucleotides in which the pseudo-nucleotides are included may be conventional DNA or RNA moieties, or may be "modified" oligomers which are those conventionally recognized in the art. For example, any of the hydroxyl groups ordinarily present may be replaced by phosphonate groups, phosphate groups, protected by standard protecting group, or activated to prepare additional linkages to additional nucleotides, or may be conjugated to solid supports. The 5′ terminal OH is conventionally phosphorylated; any 2′-OH or OH substituents at the 3′ terminus may also be phosphorylated. The hydroxyls may also be derivatized to standard protecting groups. The phosphodiester linkage shown may be replaced by alternative linking groups. These alternative linking groups include, but are not limited to embodiments wherein P(O)O is replaced by P(O)S, P(O)NR$_2$, P(O)R, P(O)OR′, CO, or CNR$_2$, wherein R is H or alkyl (1–6C) and R, is alkyl (1–6C); in addition, this group may be attached to adjacent nucleotide through O or S. Not all linkages in the same oligomer need to be identical.

"Analogous" forms of purines and pyrimidines are those generally known in the art, many of which are used as chemotherapeutic agents. An exemplary but not exhaustive list includes 4-acetylcytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5′methoxycarbonylmethyluracil, 5-methoxyuracil, 2-methylthio-N6-isopentenyladenine, uracil-5-oxyacetic acid methylester, uracil-5-oxyacetic acid (v), wybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid (v), pseudouracil, queosine, 2-thiocytosine, and 2,6-diaminopurine.

While all of the oligomers of the invention are coupled to at least one anthraquinone, it is not excluded to include in the oligonucleotide sequence additional substituents conjugated using known techniques, such as those coupled through any available OH or SH moiety, for example, at the 5′ position of RNA or DNA, the 2′ position of RNA, or an OH or SH engineered into the 5′ position of pyrimidines.

The oligomers of the invention can be synthesized using standard solid phase synthesis techniques, for example, using H-phosphonate chemistry, as described by Froehler, B., et al., *Nucleic Acids Res* (1986) 14:5399, or by the methods of Matteucci, M., et al., *J Am Chem Soc* (1981) 103:3185. In these approaches, the growing nucleotide chain is attached to solid support such as controlled-pore glass (CPG) and extended from the 3′ terminus one nucleotide at a time using a nucleotide protected in the 5′ position; followed by deprotection and addition of a subsequent nucleotide residue.

In one important approach, the anthraquinone moieties can be coupled to the oligomer of interest using initial conjugation to a pseudonucleoside or pseudonucleotide, as described in copending application U.S. Ser. No. 07/482,943, filed on even date herewith and incorporated herein by reference. Briefly, these pseudonucleosides/pseudonucleotides are achiral or are isolated enantiomers of functional group-bearing organic backbones which can be incorporated using standard techniques into the synthesis of oligonucleotides. Other methods of coupling anthraquinone to preformed oligomers are also known in the art. For example, Nelson, P. S., et al., *Nucleic Acids Res* (1989) 17:7179–7186; ibid., 7187–7194, summarize techniques which are available for incorporating functionalities into oligonucleotides in a manner that permits subsequent conjugation to other moieties such as anthraquinone. Other techniques for conjugating anthraquinone to oligonucleotide backbones include those set forth in the Background section above.

The anthraquinone substituent has the general formula

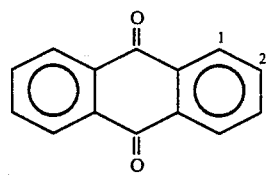

with alpha (1) and beta (2) positions noted as shown. As described above, the anthraquinone nucleus can be unsubstituted or can be substituted with one or more substituents which do not interfere with the properties conferred on the resulting oligomer by the anthraquinone nucleus. These substituents include alkyl substituents of limited number of carbons, such as 1–6C; alkynyl substituents of similar size; and these substituents optionally substituted with noninterfering functional groups. Halogens or amino substituents may also be directly substituted onto the ring.

The anthraquinone substituent is either directly bound to a functional group present on the oligonucleotide, or can be conjugated through a linker. For example, linkers which can be utilized to bind the electrophilic center at the beta position of the anthraquinone nucleus to additional functional groups on the oligomer are available from Pierce Chemical Company (Rockford, Ill.).

Any convenient method of attaching the desired anthraquinone moieties is within the scope of the invention. The oligomers of the invention contain at least one anthraquinone moiety at other than the 5′ terminus, but may contain two or more. It has been found by the inventors herein that the effects of anthraquinone moieties on hybridization strength are additive with respect to DNA hybridization, unlike those of comparable conjugates containing other substituents such as acridine derivatized to the oligonucleotide. The strengthened hybridization conferred by the anthraquinone makes these derivatized oligomers preferred drugs in antisense therapy, in particular because the specificity of the oligomer is not lost by virtue of this coupling.

Utility and Administration

Accordingly, the modified oligomers of the invention are useful in therapeutic, diagnostic and research contexts. In therapeutic applications, the oligomers are utilized in a manner appropriate for antisense therapy in general—as described above, antisense therapy as used herein includes targeting a specific DNA or RNA sequence through complementarity or through any other specific binding means, for example, sequence-specific orientation in the major groove of the DNA double-helix, or any other specific binding mode. For such therapy, the oligomers of the invention can be formulated for a variety of modes of administration, including systemic and topical or localized administration. Techniques and formulations generally may be found in *Remington's Pharmaceutical Sciences*, Mack Publishing Co., Easton, Pa., latest edition.

For systemic administration, injection is preferred, including intramuscular, intravenous, intraperitoneal, and subcutaneous. For injection, the oligomers of the invention are formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the oligomers are formulated into conventional oral administration forms such as capsules, tablets, and tonics.

For topical administration, the oligomers of the invention are formulated into ointments, salves, gels, or creams, as is generally known in the art.

In addition to use in therapy, the oligomers of the invention may be used as diagnostic reagents to detect the presence or absence of the target DNA or RNA sequences to which they specifically bind. Such diagnostic tests are conducted by hybridization through base complementarity or triple helix formation which is then detected by conventional means. For example, the oligomers may be labeled using radioactive, fluorescent, or chromogenic labels and the presence of label bound to solid support detected. Alternatively, the presence of a double or triple helix may be detected by antibodies which specifically recognize these forms. Means for conducting assays using such oligomers as probes are generally known.

In addition to the foregoing uses, the ability of the oligomers to inhibit gene expression can be verified in in vitro systems by measuring the levels of expression in recombinant systems.

It may be commented that the mechanism by which the specifically-binding oligomers of the invention interfere with or inhibit the activity of a target RNA or DNA is not always established, and is not a part of the invention. If the oligomer seeks, for example, a target mRNA, translation may be inhibited. In addition, by binding the target, the degradation of the mRNA message may be enhanced, or the further processing of the RNA may be inhibited. By formation of a triple helix, the transcription or replication of the subject DNA may be inhibited; furthermore, reverse transcription of infectious RNA or replication of infectious DNA is interfered with. It is also thought that the immune function may be modulated through physiological mechanisms similar to those induced by double-stranded RNA as exemplified by the "ampligen" system or similar to those used to suppress systemic lupus erythematosus. The oligomers of the invention are characterized by their ability to target specific oligonucleotide sequences regardless of the mechanisms of targeting or the mechanism of the effect thereof.

The following examples are intended to illustrate, but not to limit, the invention.

EXAMPLE 1

Preparation of Protected Pseudonucleoside Conjugated to Anthraquinone

A. 2-(N,N-diethanolamino)anthraquinone was prepared as follows. A mixture of 2-chloroanthraquinone (2.42 g; 10 nmole) and an excess of diethanolamine in DMSO (20 ml) was heated to 150° C. After 24 hours reaction, the reaction mixture was cooled to room temperature, then poured into water (70 ml). The red precipitate was filtered off, washed thoroughly with water, and dried in air. The crude product, containing some starting material, was used for the protection reaction of paragraph B without further purification.

B. The crude compound prepared in paragraph A, was dissolved in pyridine (20 ml) and triethyl amine (1.7 ml), cooled to 0° C., followed by addition of DMAP (0.2 g) and DMT-Cl (4.0 g; 12 mmol). The reaction mixture was warmed to room temperature. After 4 hours of reaction, more DMT-Cl (1 g) was added to the reaction mixture and reacted one more hour, then concentrated to dryness. The residue was then partitioned between methylene chloride and saturated sodium bicarbonate solution. The organic solution was separated and dried, purified by flash column chromatography on silica gel, eluted with 1% $Et_3N$/1% $CH_3OH/CH_2Cl_2$, to afford the product mono-DMT-protected 2-N,N-diethanolaminoanthraquinone, in an amount of 0.7 g (13% overall yield); 3.1 g of unreacted starting material was recovered.

EXAMPLE 2

Conjugation to CPG Support

A. A mixture of the DMT-protected anthraquinone pseudonucleoside of Example 1, paragraph B (0.5 g; 0.81 mmol), DMAP (0.1 g) and succinic anhydride (0.326 g; 3.26 mmol) in pyridine (10 ml) was stirred at room temperature for 4 hours, and more succinic anhydride (0.1 g) was added to the reaction. After 2 more hours of reaction, the residue was dissolved in methylene chloride, washed with 1M TEAB aqueous solution. The organic solution was isolated, dried over $Na_2SO_4$, concentrated, then purified by flash column chromatography, and eluted with 1% $Et_3N$/2%

$CH_3OH/CH_2Cl_2$, 1% $Et_3N/5\%$ $CH_3OH/CH_2CH_2$, to afford the succinylated product. The succinylated form of the subject compound (0.39 g) was isolated as a red solid (yield 59%).

B. After succinylation as described in paragraph A, 3–5 equivalents of the succinylated pseudonucleoside, 10 equivalents of diisopropylcarbodiimide, a catalytic amount of DMAP and CPG in DMF/pyridine (4/1; 4 ml/g CPG) were shaken at room temperature overnight and then capped with acetic anhydride and pyridine. After 4 hours capping at room temperature, quenching by slow addition of methanol, CPG was filtered off and washed thoroughly with methylene chloride, methanol, and ether, and dried under vacuum overnight. The resulting CPG derivative with anthraquinone-coupled pseudonucleoside are then used to provide the pseudonucleotide.

EXAMPLE 3

Phosphorylation of Mono-DMT-Protected Pseudonucleosides

To a cold methylene chloride solution (8 ml; 0° C.) of the DMT-protected anthraquinone pseudonucleoside of Example 1 paragraph B (0.24 g; 0.39 mmol) were added pyridine (0.1 ml) and 2-chloro-4H-1,2,3-benzodioxa-phos-phorin-4-one (1.17 ml of 1M methylene chloride solution; 1.17 mmol). After 0.5 hours of reaction at 0° C., the reaction mixture was washed with 1M TEAB aqueous solution. The organic solution was separated, dried over $Na_2SO_4$, and concentrated. The residue was purified by flash column chromatography, eluted with 1.5% $Et_3N/5\%$ $CH_3OH/CH_2Cl_2$. Fractions of the product were combined, washed with 1M TEAB aqueous solution, dried over $Na_2SO_4$, and concentrated, affording phosphorylated DMT-protected anthraquinone pseudonucleotide.

EXAMPLE 4

Synthesis of Oligomers

The protected anthraquinone-coupled pseudonucleosides of Examples 2 and 3 were then utilized in standard solid-phase oligomer synthesis techniques, as described in *Oligonucleotide Synthesis—A Practical Approach*, Gait, M. J., ed. (1984) IRL Press, Ltd.

EXAMPLE 5

Properties of Oligomers Coupled to Anthraquinone

The oligomers shown below were synthesized and tested for stability in vitro and in vivo, and specificity of hybridization to complementary DNA and RNA. The oligomers prepared are as follows, where "P" represents the pseudonucleotide anthraquinone-containing residue.

Table 1 above gives the results with respect to stability of hybridization to complement as a difference in melting point, as compared to the control lacking the inclusion of the pseudonucleotide of the invention. As seen from the table, hybridization is increased with respect to DNA and RNA complement in almost all cases. It is seen that the oligomers which contain two anthraquinone modifications, generally, show cumulatively enhanced stability as compared to those containing only one such residue.

In a manner similar to that set forth in Examples 1–4 above, oligomers were constructed which include as "P*", the pseudonucleoside $HO(CH_2)_6NH(CH_2)_6OH$ wherein the nitrogen is substituted with anthraquinone at the beta position. These analogs were tested for stability of hybridization with complementary RNA. The results, shown in Table 2, indicate the longer methylene chains in the pseudonucleoside do not result in enhanced stability as compared to the diethanolamine pseudobases.

TABLE 2

| Oligomer | | Tm, °C. | ΔT, °C. |
|---|---|---|---|
| 1* | 5'-CCC-TCT-CTT-TTT-CCP* | 64.0 | 4.0 |
| 2* | 5'-CCC-TCT-P*CT-TTT-TCC | 57.5 | −2.5 |
| 4* | 5'-P*CC-CTC-TCT-TTT-TCC | 63.5 | 3.5 |
| 5* | 5'-CCC-TCT-P*CT-TTT-TCC-P* | 58.5 | −1.5 |
| 6* | 5'-P*CC-CTC-TCT-TTT-TCC-P* | 65.0 | 5.0 |
| Control | 5'-CCC-TCT-CTT-TTT-CC | 60.0 | 0 |

Stability to Nuclease Degradation

The stability of the modified oligonucleotides to lysis was tested under conditions which simulate in vitro cell culture and typical in vivo environments. The oligomer, 5'-TTT-TTC-TCC-ATP, wherein P represents diethanolamine pseudonucleoside derivatized to anthraquinone was prepared, as described in Examples 1–4. The control is of the formula 5'-TTT-TTC-TCC-AT.

These oligonucleotides were treated with snake venom phosphodiesterase, under conditions where the control is completely degraded within 5 minutes. Approximately 90% of the modified oligomer remained intact at 5 minutes. Table 3 shows the comparative stability of the control and modified oligomer in RPMI+10% heat-inactivated fetal calf serum; the data are given as % oligomer remaining at the noted times. It is clear that derivatization to anthraquinone enhances stability.

TABLE 3

| | 0 hr | 1 hr | 3 hr | 6 hr |
|---|---|---|---|---|
| Control | 100% | 0% | 0% | 0% |

TABLE 1

| Oligomer No. | Oligomer | ΔT, °C. DNA$^a$ | ΔT, °C. RNA$^b$ | Tm, °C. RNA$^b$ | Tm, °C. DNA$^a$ | Control |
|---|---|---|---|---|---|---|
| 1 | 5'-CCC-TCT-CTT-TTT-CCP | +4.5 | +4.0 | 64.0 | 56.5 | (52) |
| 2 | 5'-CCC-TCT-PCT-TTT-TCC | +3.0 | −0.5 | 59.5 | 55.0 | (52) |
| 3 | 5'-CCC-TCT-CPT-TTT-TCC | +2.5 | −0.5 | 59.5 | 54.5 | (52) |
| 4 | 5'-PCC-CTC-TCT-TTT-TCC | +5.0 | +4.0 | 64.0 | 59.0 | (52) |
| 5 | 5'-CCC-TCT-PCT-TTT-TCC-P | +7.5 | +4.0 | 64.0 | 59.5 | (52) |
| 6 | 5'-PCC-CTC-TCT-TTT-TCC-P | +9.0 | +8.0 | 68.0 | 61.0 | (51.5) |
| 7 | 5'-PCC-CTC-TPC-TTT-TTC-CP | +11.0 | +7.5 | 67.5 | 63.0 | (51.5) |
| Control | 5'-CCC-TCT-CTT-TTT-CC | 0 | 0 | 60.0 | 52.0 | |

$^a$~5 μM DNA/DNA (1/1) in 150 mM NaCl/10 mM $Na_2HPO_4$, pH 7.5
$^b$~1.6 μM DNA/RNA (1/1) in 150 mM NaCl/50 mM Tris, pH 7.5

TABLE 3-continued

|  | 0 hr | 1 hr | 3 hr | 6 hr |
|---|---|---|---|---|
| Anthraquinone | 100% | 90% | 60% | 50% |

Specificity of Hybridization

The oligomers containing anthraquinone-conjugated pseudonucleotides were evaluated with regard to specificity in comparison to controls. Hybrid oligomer/single-strand RNA complexes were examined. As shown in Table 4 below, a single basepair mismatch has a comparable effect on the melting temperature of the oligomer whether or not the oligomer is coupled to anthraquinone. In the first set of controls, a single basepair mismatch in the middle of the sequence lowers the melting temperature by about 8° C. in the controls; a similar melting point lowering is achieved in the presence of two anthraquinone residues.

Similarly, when the mismatch is at the 3' end, the presence of the anthraquinone residue enhances the discrimination of a mismatch thereby improving the specificity. However, the anthraquinone moiety enhances the discrimination of a mismatch, thereby improving the specificity of hybridization.

TABLE 4

|  | Tm, °C. | ΔT, °C. |
|---|---|---|
| Effect of Mismatch on Controls: | | |
| 5'-CCC-TCT-CTT-TTT-CC | 60.5 | — |
| 5'-T-CCC-TCT-CTT-TTT-CC | 61.0 | +0.5 |
| 5'-CCC-TCT-TTT-TTT-CC | 52.5 | −8.0 |
| Effect of Mismatch with Anthraquinone: | | |
| 5'-P-CCC-TCT-CTT-TTT-CCP | 68.0 | — |
| 5'-P-CCC-TCT-TTT-TTT-CCP | 60.5 | −7.5 |
| Effect of 3'-Terminal Mismatch on Control: | | |
| 5'-CCC-TCT-CTT-TTT-CC | 60.0 | — |
| 5'-CCC-TCT-CTT-TTT-CT | 57.5 | −2.5 |
| Effect of 3'-Terminal Mismatch with Anthraquinone: | | |
| 5'-CCC-TCT-CTT-TTT-CC-P | 64 | — |
| 5'-CCC-TCT-CTT-TTT-CT-P | 59.5 | −4.5 |

We claim:

1. A modified oligonucleotide wherein said modification comprises at least one substituted or unsubstituted anthraquinone residue conjugated to a pseudonucleoside.

2. The oligonucleotide of claim 1 wherein said conjugation is through the β-position of the anthraquinone residue.

3. The oligonucleotide of claim 1 wherein the anthraquinone residue is unsubstituted.

4. The oligonucleotide of claim 1 wherein said modification comprises at least two anthraquinone residues.

5. A pharmaceutical composition for treating diseases or conditions characterized by the presence of unwanted DNA or RNA which contains, as active ingredient, an effective amount of the oligonucleotide of claim 1.

* * * * *